United States Patent [19]
Tockweiler et al.

[11] Patent Number: 6,074,388
[45] Date of Patent: Jun. 13, 2000

[54] ELECTRICALLY OPERATED MEDICAL APPARATUS

[75] Inventors: Udo Tockweiler; Bertram Schilling, both of Immendingen, Germany

[73] Assignee: Gebrueder Berchtold GmbH & Co., KG, Tuttlingen, Germany

[21] Appl. No.: 09/115,494

[22] Filed: Jul. 14, 1998

[30] Foreign Application Priority Data

Jul. 16, 1997 [DE] Germany .......................... 197 30 456

[51] Int. Cl.⁷ .................................................. A61B 18/04
[52] U.S. Cl. ................................................ 606/34; 606/1
[58] Field of Search ............................. 128/903; 606/32, 606/33, 34

[56] References Cited

U.S. PATENT DOCUMENTS

| | | | |
|---|---|---|---|
| 4,184,510 | 1/1980 | Murry et al. | 137/565 |
| 4,696,309 | 9/1987 | Stephan . | |
| 5,351,187 | 9/1994 | Hassett | 705/13 |
| 5,396,538 | 3/1995 | Hong | 455/573 |
| 5,431,645 | 7/1995 | Smith et al. | 606/1 |
| 5,561,699 | 10/1996 | Fenner . | |

FOREIGN PATENT DOCUMENTS

| | | |
|---|---|---|
| 0424687A1 | 5/1991 | European Pat. Off. . |
| 0424792A1 | 5/1991 | European Pat. Off. . |
| 4125313A1 | 2/1993 | Germany . |

*Primary Examiner*—Michael Peffley
*Attorney, Agent, or Firm*—Townsend and Townsend and Crew LLP

[57] ABSTRACT

The invention relates to an electrically operated medical apparatus, such as an electro-surgical apparatus comprising an electrical instrument which can be handled by a person and which is connectable or connected to an electrically operated feed and control apparatus, such as a high-frequency surgical apparatus, which is connected to a switch to be actuated by the person, by means of which a switching signal initiated by him can switch on and off one or more functions of the electrical instrument in the feed and control apparatus. In accordance with the present teaching, the switch is associated with a transmitter part which converts the switching signals into signals which can be transmitted without wires and which are transmitted via a transmitting element to a receiving element of a receiving station. The receiving element is connected to the switching input of the feed and control apparatus and transmits to the feed and control apparatus a control signal corresponding to the switching signal.

23 Claims, 1 Drawing Sheet

ELECTRICALLY OPERATED MEDICAL APPARATUS

1. FIELD OF THE INVENTION

The invention relates to an electrically operated medical apparatus, such as an electro-surgical apparatus, comprising an electrical instrument which can be handled by a person and which is connectable or connected to an electrically operated feed and control apparatus, such as a high-frequency surgical apparatus, which is connected to a switch to be actuated by the person, by means of which a switching signal initiated by him can switch on and off one or more functions of the electrical instrument in the feed and control apparatus.

2. DESCRIPTION OF THE PRIOR ART

In operating theaters, many pieces of electrical operating apparatuses are used, in which electrical leads or hose connections have to be present between the patient and the apparatus. Since space problems always exist around the operating table during an operation, such lines and connections are very disturbing. Particularly critical are connection lines which are laid along the floor beneath the operating table, such as feed lines to foot switches, via which the surgeon can control apparatus functions, for example within a high-frequency surgical apparatus. The foot operation is often necessary because the surgeon requires both hands to manipulate the instruments, of which at least one is connected to the electrical feed and control apparatus. Since the electrically operated pieces of medical apparatuses are generally accommodated at a certain distance from the operating table for space reasons, the lines on the floor must be relatively long so that they hinder the free mobility of the people standing around the operating table.

BRIEF SUMMARY OF THE INVENTION

The object of the invention is to so design an electrically operated medical apparatus of the initially named kind that the effort required for the laying of the lines is minimized, so that, in particular in the critical region beneath and around the operating table, disturbances due to lines laid there are largely avoided.

In order to satisfy this object, the present invention provides an apparatus of the initially named kind wherein the switch is associated with a transmitter part which converts the switching signals into signals which can be transmitted without wires and which are transmitted via a transmitting element to a receiving element of a receiving station, which is connected to the switching input of the feed and control apparatus and transmits a control signal corresponding to the switching signal to the feed and control apparatus. It is particularly preferred when the signals that are transmitted free of wires are infrared, ultrasonic or radiofrequency signals. The switch is conveniently a foot switch.

Thus, in accordance with the invention, one dispenses fully with connection lines between the switch which is in particular, formed as foot switches and a receiving station which is preferably arranged close to the feed and control apparatus, so that the relevant hindrances for the people working at the operating table are fully avoided.

A special problem with pieces of electrically operated medical surgical apparatuses lies in the fact that the reliability of the transmission against disturbances must be very high. This is particularly difficult to realize in operating theaters because numerous potentially disturbing devices, such as high-frequency surgical apparatuses, X-ray apparatuses, NMA tomographs or similar complicated electronic apparatuses, can be present there, against which absolute reliability against disturbance must be ensured. The transmission must, even in the non-disturbed state, be so reliable that only the function which the surgeon selects via the foot switch is switched on with high reliability. A further problem results if foot switches of the inventive kind are possibly used in two neighboring operating theaters, since their mutual disturbance must be precluded. An advantageous further development of the invention in this respect is characterized wherein a switching signal conversion stage is provided in the transmitter part, which converts the switching signals received from the switch into a digitized signal which can be transmitted without wires and the signals to be transmitted without wires are preferably codable or coded.

Through the digitalization or codability of the transmitted signals, disturbing influences, such as mutual influences of adjacently operated foot switches, can be fully precluded.

In one embodiment the transmitter part is directly incorporated into the foot switch itself which is particularly advantageous. As a result of modern electronic components, a foot switch can thus be provided which is practically not distinguished from a foot switch with transmission via a line, but which enables a wire-free transmission of the switching signals to the receiving station.

In order to ensure complete independence of the switch that is used in accordance with the invention from any form of external energy sources, the operating preferably takes place wherein the transmitter is operated by means of battery or rechargeable accumulators.

In order to overcome problems of impending emptying of the batteries or accumulators, it is expedient when an alarm indicator is built into the transmitter part and responds in good time before the discharge of the batteries or accumulators and transmit them from an alarm signal. A reserve battery or a reserve accumulator is preferably provided in the transmitter part and, with extensive discharge of the main battery or of the main accumulator, automatically takes on the feeding of the transmitter part.

Since medical feed and control apparatuses, such as electro-surgical apparatuses, have a normal plug input for a switch, in particular a foot switch, it is expedient when, in accordance with the invention, one proceeds in such a way that the line leading from the receiving station to the feed and control apparatus has a plug contact or a socket at its end, which corresponds to that of a line coming from a customary switch, particularly from a foot switch.

The receiving station can then be connected to the switching input of the feed and control apparatus in precisely the same way as a customary foot switch.

Alternatively, the receiving station could also be incorporated into the feed and control apparatus.

Since no physical connection exists between the transmitter part and the receiving station, an embodiment in which the receiving station has a holder for the transmitter part when it is not in use is advantageous. Thus, the transmitter part and the receiving station in any case form a physical unit when not in use.

A charging apparatus should be provided for the recharging of accumulators provided in the transmitter part. This can be achieved wherein the transmitter part and/or the receiving station has a charging apparatus for the accumulators in the transmitter part. For the purpose of the power supply of the charging apparatus, it is expedient when the receiving station is directly connectable to the power mains in a mains connection lead or via the feed and control apparatus.

A largely automatic charging up of the accumulators in the transmitter part is achieved by apparatuses in which, when the transmitter part is in its holder, in particular at the receiving station, the accumulator or accumulators of the transmitter part are automatically charged up. When the transmitter part is held at the receiving station during non-use, charging connections on the transmitter part can come into electrical contact with counter-connections at the receiving station. That is to say, when the transmitter part is in the holder at the receiving station during non-use, the receiving station can be coupled inductively to a charging apparatus in the transmitter part for the charging up of the accumulators.

An apparatus in which the output signals of a plurality of different transmitters are so coded that they do not mutually influence one another, and in which the receiving station has a corresponding signal recognition stage, is particularly advantageous in order to reliably recognize transmission signals which have been disturbed by external influences.

An embodiment in which the receiving station can be connected by means of a plug contact directly to the input of the feed and control apparatus, which is provided for the plug contact of a conventional foot switch is particularly advantageous, since in this case the receiving station only needs to be plugged into the receiving socket of a conventional foot switch in order to produce the required connection between the foot switch at the transmitter part with the feed and control apparatus.

Since the receiving station of the invention can be of very small dimensions, it is expedient to provide a separate charging station for the transmitter part, which can be arranged at a suitable position and optionally relatively far removed from the receiving station. The charging station should have a holder for the transmitter part, so that the latter can be attached there when not in use and a charging up of the accumulators can take place in the period of non-use.

DETAILED DESCRIPTION OF THE PREFERRED EXEMPLARY EMBODIMENT

Figure 1:
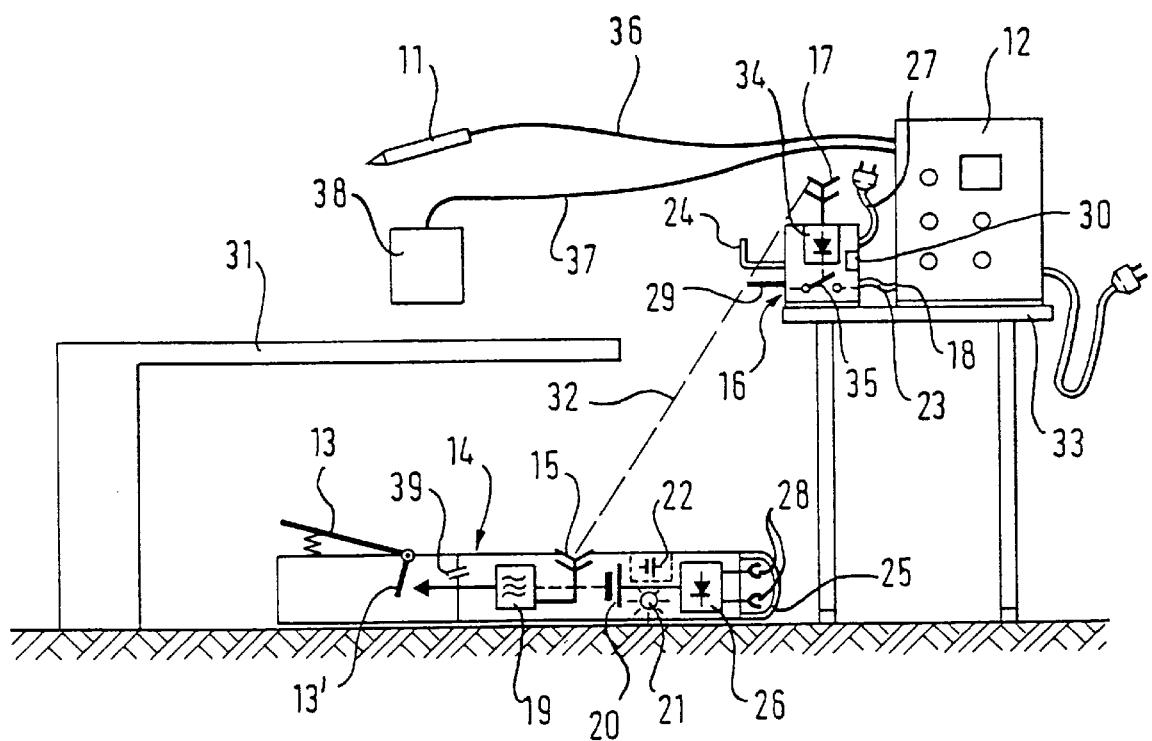
FIG. 1 is a schematic illustration of a high-frequency surgical apparatus connected in accordance with the invention in an arrangement at a medical operating table.

In accordance with FIG. 1, a serving table 33, on which a high-frequency surgical apparatus 12 is located, is arranged alongside an operating table 31 provided in an operating theater. A foot switch 13 is provided on the floor beneath the operating table and can be pressed down by the surgeon working at the operating table 31 and caused to electrically close or open a pair of switch contacts 13'.

In accordance with the invention, the foot switch 13 is a component of a transmitter part 14, which has a switching signal conversion stage 19 connected to the switch contact pair 13'. A corresponding, digitized, high-frequency signal can be produced in the switching signal conversion stage 19 on closing of the switch contact pair 13', with this signal then being transmitted via a transmitter antenna 15 provided in the transmitter part 14 over a transmission path 32 indicated in broken lines, without the use of a wire, to the receiving aerial 17 of a receiving station 16, which is accommodated at a suitable position in the operating theater.

The electrical feeding of the switching signal conversion stage 19 in the transmitter part 14 takes place via an accumulator 20, which can be charged up by a charging apparatus 26. Furthermore, within the transmitter part 14, there is a reserve accumulator 22 which is automatically connected, on discharge of the main accumulator 20, with the switching signal conversion stage 19 in order to take on the electrical feeding of the switching signal conversion stage 19.

An alarm indicator 21, in particular an acoustic alarm within the transmitter part 14 responds when the main accumulator 20 is discharged and the reserve accumulator 22 has taken over the feeding.

Two charging connections 28, by which the charging apparatus 26 can be supplied with electrical energy, lead from the charging apparatus 26 to the outside of the transmitter part 14.

The receiving station 16 has a demodulator 34 connected to the receiving antenna 17, which demodulates the received signal and correspondingly actuates a switch 35 provided in the receiving station 16. In this manner, the switch 35 carries out the same switching procedures as the switch contact pair 13' of the foot switch 13. A control line 23 branches off from the receiving station 16, which is connected via a mains connection line 27 to the power mains in a non-illustrated manner. The control line 23 leads to a feed and control apparatus in the form of a radiofrequency surgical apparatus 12 and is connected to its foot switch switching input 18 as a result of a correspondingly designed coupling element. The switch 35 of the receiving station 16 brings about the same switching procedures in the high-frequency surgical apparatus 12, as if a customary foot switch 13 is directly connected via a switch line to the switch input 18.

High-frequency lines 36, 37 respectively extend from the high-frequency surgical apparatus 12 to a high-frequency surgical electrical instrument 11, which is to be operated by the surgeon and to a neutral electrode 38, which is to be brought into electrically conducting contact with a patient located on the operating table 31.

In the receiving station 16 there is, moreover, a signal recognition stage 30, which enables the transmission signals disturbed on the transmission path 32 to still be largely recognized.

At the receiving station 16 there is located a holder 24, on which the foot switch 13 can be suspended when not in use by means of a hoop 25.

During this, the charging connections 28 of the transmitter part 14 automatically enter into electrically conducting contact with the counter-connections 29 of the receiving station 16, which automatically ensure a charging up of the accumulators 20 and 22 in the transmitter part 14 via the charging connections as long as the receiving station 16 is connected to the power mains via the mains connection line 27. On renewed use of the foot switch 13 it is thus automatically ensured that both accumulators 20, 22 are in the fully charged state.

In order not to have to interrupt the operation procedure in the event that both accumulators 20, 22 are discharged during an operation, a second foot switch 13 with an identically designed transmitter part 14 can be made available in accordance with the invention. It is also possible for the foot switch part and the transmitter part 14 to be connected to one another via a separable interface, which is schematically illustrated in FIG. 1, so that in the event of a discharge of the accumulators 20, 22 the foot switch part can be separated at the separating point 39 from the transmitter part, whereupon a second transmitter part, which is kept available, can be plugged in there, whereby the foot switch 13 is again fully prepared for operation.

When not in use, the transmitter part 14 does not need to be suspended on the receiving station 16 but can be suspended on a charging station secured somewhere to the wall. This embodiment is preferred because the receiving station 16 can be made of very small dimensions and thus, for example, also can be built in to the high-frequency surgical apparatus 12. It is also conceivable to connect the receiving station 16 through a plug adapter to the high-frequency surgical apparatus 12. If desired, this can be effected at the receiving socket for the cable of a conventional foot switch wherein the receiving station 16 delivers an output signal in the same way as a conventional foot switch. It is also of particular significance for the invention that the plug of a conventional foot switch is retained and is simply connected to the receiving station 16 having the switch 35 at its output rather than to a conventional foot switch. This design is of particular importance because, should a failure of the transmitter part 14 of the invention occur, a conventional foot switch can at once be connected to the apparatus 12.

What is claimed is:

1. An electrically operated medical apparatus comprising an electrical instrument which can be handled by a person and which is connected to an electrically operated feed and control apparatus, which is connected to a switch to be actuated by the person, by means of which a switching signal initiated by the person can switch on and off one or more functions of the electrical instrument in the feed and control apparatus, wherein the switch is associated with a transmitter part which converts the switching signals into signals which can be transmitted without wires and which are transmitted via a transmitting element to a receiving element of a receiving station, which is connected to a switching input of the feed and control apparatus and transmits a control signal corresponding to the switching signal to the feed and control apparatus, wherein the receiving station is connected to the feed and control apparatus via a connection that is configured such that upon removal of the connection, a customary switch may be connected to the feed and control apparatus in place of the receiving station.

2. An apparatus in accordance with claim 1, wherein the signals transmitted free of wire are one of infrared, ultrasonic or high-frequency (radiofrequency) signals.

3. An apparatus in accordance with claim 1, wherein the switch is a foot switch.

4. An apparatus in accordance with claim 1, wherein a switching signal conversion stage is provided in the transmitter part, which converts the switching signals received from the switch into a digitized signal which can be transmitted without wire.

5. An apparatus in accordance with claim 1, wherein signals transmitted without a wire can be coded.

6. An apparatus in accordance with claim 5 wherein the signals transmitted without a wire are coded.

7. An apparatus in accordance with claim 1, wherein the switch is a component of the transmitter part.

8. An apparatus in accordance with claim 1, wherein the transmitter part is operated by means of one of a main battery or main rechargeable accumulators.

9. An apparatus in accordance with claim 8, wherein an alarm indicator is built into the transmitter part and responds and transmits an alarm signal in good time before discharge of the main battery or main accumulators.

10. An apparatus in accordance with claim 8, wherein one of a reserve battery or reserve accumulator is provided in the transmitter part and, on extensive discharge of the main battery or the main accumulators, automatically takes on the feeding of the transmitter part.

11. An apparatus in accordance with claim 1, wherein the receiving station has a holder for the transmitter part when it is not in use.

12. An apparatus in accordance with claim 1, wherein the transmitter part includes at least one accumulator and at least one of the transmitter part and the receiving station has a charging apparatus for the at least one accumulator in the transmitter part.

13. An apparatus in accordance with claim 12, wherein the receiving station can be connected directly via one of a mains connection lead or the feed and control apparatus to the power mains.

14. An apparatus in accordance with claim 11, wherein the transmitter part includes at least one accumulator and when the transmitter part is in its holder the at least one accumulator of the transmitter part (14) are automatically charged up.

15. An apparatus in accordance with claim 14, wherein when the transmitter part is held at the receiving station during non-use, charging connections on the transmitter part come into electrical contact with counter-connections at the receiving station.

16. An apparatus in accordance with claim 14, wherein when the transmitter part is in the holder at the receiving station during non-use, the receiving station is coupled inductively to a charging apparatus in the transmitter part for the charging up of the at least one accumulator.

17. An apparatus in accordance with claim 14 wherein the transmitter part is in its holder at the receiving station.

18. An apparatus in accordance with claim 1, wherein output signals of a plurality of different transmitters are so coded that they do not mutually influence one another and the receiving station has a corresponding signal recognition stage.

19. An apparatus in accordance with claim 1, wherein the transmitter part includes at least one accumulator and a charging station for the transmitter part is provided separately from the receiving station at a suitable position, and the transmitter part is held when not used by the charging station, in order to effect the charging up of the at least one accumulator.

20. An apparatus in accordance with claim 1 wherein the customary switch is a foot switch.

21. An apparatus in accordance with claim 1 wherein the connection for connecting the receiving station to the feed and control apparatus is a plug contact that is provided for a plug contact of a conventional foot switch.

22. An electrically operated medical apparatus comprising an electrical instrument which can be handled by a person and which is connected to an electrically operated feed and control apparatus, which is connected to a switch to be actuated by the person, by means of which a switching signal initiated by him can switch on and off one or more functions of the electrical instrument in the feed and control apparatus, wherein the switch is associated with a transmitter part which converts the switching signals into signals which can be transmitted without wires and which are transmitted via a transmitting element to a receiving element of a receiving station, which is connected to a switching input of the feed and control apparatus and transmits a control signal corresponding to the switching signal to the feed and control apparatus, wherein the transmitter part includes at least one accumulator and at least one of the transmitter part and the receiving station has a charging apparatus for the at least one accumulator in the transmitter part, and wherein the receiving station can be connected directly via one of a mains connection lead or the feed and control apparatus to the power mains.

23. An electrically operated medical apparatus comprising an electrical instrument which can be handled by a person and which is connected to an electrically operated feed and control apparatus, which is connected to a switch to be actuated by the person, by means of which a switching signal initiated by the person can switch on and off one or more functions of the electrical instrument in the feed and control apparatus, wherein the switch is associated with a transmitter part which converts the switching signals into signals which can be transmitted without wires and which are transmitted via a transmitting element to a receiving element of a receiving station, which is connected to a switching input of the feed and control apparatus and transmits a control signal corresponding to the switching signal to the feed and control apparatus, wherein the transmitter part includes at least one accumulator and a charging station for the transmitter part is provided separately from the receiving station at a suitable position, and wherein the transmitter part is held when not used by the charging station in order to effect the charging up of the at least one accumulator.

* * * * *